(12) United States Patent
Schönlein et al.

(10) Patent No.: US 7,118,271 B2
(45) Date of Patent: Oct. 10, 2006

(54) CALIBRATING TEMPERATURE SENSORS OF WEATHERING DEVICES BY MEANS OF CONTACTLESS TEMPERATURE MEASUREMENT

(75) Inventors: Artur Schönlein, Rüsselsheim (DE); Martin Dickert, Gelnhausen/Höchst (DE)

(73) Assignee: Atlas Material Testing Technology GmbH, (DE)

( * ) Notice: Subject to any disclaimer, the term of this patent is extended or adjusted under 35 U.S.C. 154(b) by 0 days.

(21) Appl. No.: 10/893,895

(22) Filed: Jul. 20, 2004

(65) Prior Publication Data

US 2005/0018744 A1    Jan. 27, 2005

(30) Foreign Application Priority Data

Jul. 24, 2003    (DE) ................. 103 33 774

(51) Int. Cl.
*G01K 15/00*    (2006.01)
*G01K 19/00*    (2006.01)

(52) U.S. Cl. ................. 374/2; 374/9; 374/121
(58) Field of Classification Search .......... 374/2, 374/9, 4–7, 121
See application file for complete search history.

(56) References Cited

U.S. PATENT DOCUMENTS

| | | | | |
|---|---|---|---|---|
| 3,309,881 A | * | 3/1967 | Beerman .................... | 374/2 |
| 3,664,188 A | * | 5/1972 | Kockott .................... | 73/150 R |
| 4,172,383 A | * | 10/1979 | Iuchi ..................... | 374/9 |
| 4,627,287 A | * | 12/1986 | Suga ..................... | 73/865.6 |
| 4,984,902 A | | 1/1991 | Crowley et al. | |
| 5,128,884 A | * | 7/1992 | Prager ................... | 702/99 |
| 5,206,518 A | * | 4/1993 | Fedor et al. ............ | 250/504 R |
| 5,220,840 A | | 6/1993 | Neigoff et al. | |
| 5,305,634 A | * | 4/1994 | Suga et al. ............. | 73/86 |
| 6,004,029 A | * | 12/1999 | Moslehi et al. ........ | 374/1 |
| 6,720,562 B1 | * | 4/2004 | Rathod et al. .......... | 250/395 |
| 6,742,925 B1 | * | 6/2004 | Maccarone ............. | 374/2 |
| 2003/0095583 A1 | * | 5/2003 | Maccarone ............. | 374/2 |
| 2003/0214996 A1 | | 11/2003 | Hardcastle, III | |

FOREIGN PATENT DOCUMENTS

DE    196 81 502 T1    3/1999

(Continued)

OTHER PUBLICATIONS

Webpage of Dataforth; www.sensor-interface.de/dscp80.html; Feb. 17, 2006.

(Continued)

*Primary Examiner*—Yaritza Guadalupe McCall
(74) *Attorney, Agent, or Firm*—Vedder Price Kaufman & Kammholz

(57) ABSTRACT

Calibrating temperature sensors of weathering devices by means of contactless temperature measurement A temperature sensor (10) which is, for example, designed as a black standard sensor and is typically used in apparatuses for artificial weathering of material samples, has in a known way a stainless steel plate (1) which is provided with a black coating (2) and is thermally coupled at its rear side to a platinum resistor (3). The output signal of the electric measurement transducer circuit connected to the platinum resistor (3) by means of feeder wires (4) can be calibrated with the surface temperature measured in a contactless fashion by a pyrometer (8). The calibration operation can be carried out under the conditions prevailing in a weathering device, that is to say while applying to the surface of the sensor the optical radiation of a xenon radiation source (7) and an airstream (9) parallel to the surface.

14 Claims, 4 Drawing Sheets

FOREIGN PATENT DOCUMENTS

Figure 1:
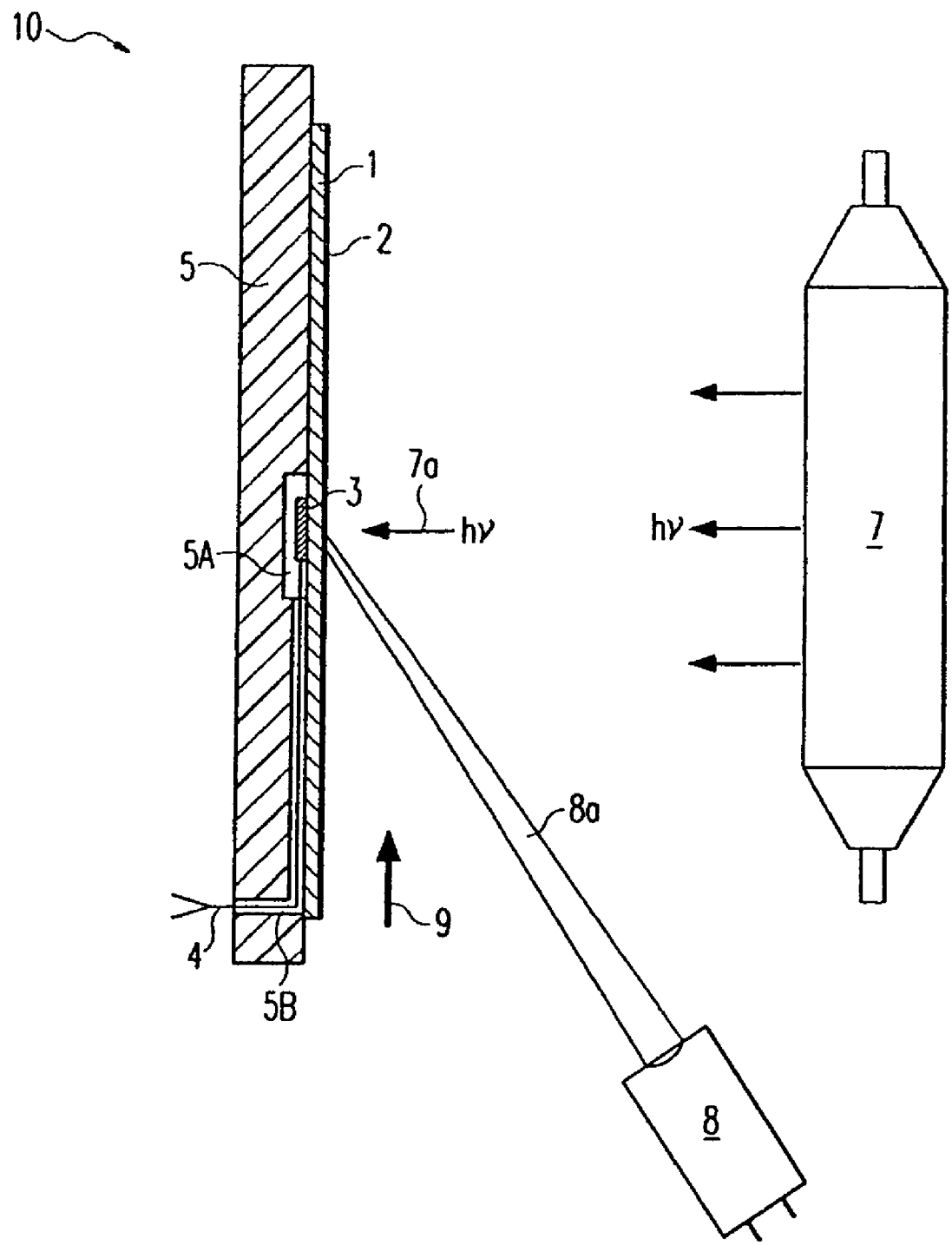

| | | |
|---|---|---|
| EP | 0 320 209 A2 | 6/1989 |
| EP | 1 248 097 A1 | 10/2002 |
| JP | 63094133 A * | 4/1988 |
| WO | WO 94/27124 | 11/1994 |

OTHER PUBLICATIONS

Dataforth 2004 catalog directed to DSCP80 Programmable Temperature Transmitter, DIN Mount, pp. 183-187.

Dataforth 2004 catalog directed to DSCL, DSCP, SCTP, Industrial Loop Isolators and Transmitters; pp. 160-161.

* cited by examiner

CALIBRATING TEMPERATURE SENSORS OF WEATHERING DEVICES BY MEANS OF CONTACTLESS TEMPERATURE MEASUREMENT

Calibrating temperature sensors of weathering devices by means of contactless temperature measurement The present invention relates to a method for calibrating temperature sensors as used, in particular, in apparatuses for artificial weathering of samples. Such temperature sensors are known under the designations of black panel sensor, black standard sensor or white standard sensor. The invention further relates to an apparatus for carrying out the calibration method.

In apparatuses for artificial weathering of material samples, the aim is to estimate the service life of materials which are permanently exposed during use to the natural weathering conditions and therefore worsen under climatic influences such as sunlight, solar heat, moisture and the like. In order to obtain a good simulation of the natural weathering conditions, the spectral energy distribution of the light generated in the apparatus must correspond as far as possible to that of the natural solar radiation, for which reason xenon radiators are used as radiation sources in such devices. An accelerating ageing test of the materials is achieved essentially by radiating the samples much more intensively by comparison with the natural conditions, this radiation accelerating the ageing of the samples. It is therefore possible after a relatively short time to pronounce on the long-term ageing behaviour of a material sample.

A majority of the samples investigated in artificial weathering devices consist of polymer materials. With these, the weathering-induced deterioration is substantially produced by the UV fraction of the solar radiation. The photochemical primary processes proceeding in the process, that is to say the absorption or photons and the generation of excited states or free radicals, are not a function of temperature. By contrast, the subsequent reaction steps with the polymers or additives are a function of temperature, and so the observed ageing of the materials is likewise a function of temperature. The degree of the temperature dependence is a function of the material and of the change in property being observed.

In order to take account of this fact, the room temperature and/or the sample temperature are/is generally kept constant during the artificial weathering of polymer materials. Because of the temperature dependence of the ageing, it is necessary for the temperatures to be known and kept constant in order to be able to intercompare the results of different weathering runs.

Since direct measurement of the sample temperature of the material samples to be investigated is a problem, use is made in weathering devices of temperature sensors whose measured temperature is employed as a measure of the sample temperature. A black panel sensor, for example, can be used as such a temperature sensor. In the printed publication EP 0 320 209 A2, a weathering device is described which has a weathering chamber in which a xenon lamp is provided as light source for outputting light of a predetermined intensity. Located inside the weathering chamber is a cylindrically symmetrical sample holder frame which can be rotated about the light source. This sample holder frame carries both material samples to be investigated and black panel sensors. The material samples and black panel sensors are therefore exposed under the same conditions to the radiation field of the light source and the remaining conditions set inside the weathering chamber. In order to be able to control the sample temperature within specific limits, and homogenize it inside the weathering chamber, an airstream is additionally introduced into the weathering chamber and flows past the sample holder frame and the material samples and black panel sensors, which are held therein, in a cylindrical symmetrical fashion with reference to the light source. The airstream in this case dissipates a portion of the heat from the material samples and black panel sensors. This can be utilized for temperature control by using the temperature measured by the black panel sensors as a control signal for the strength of the airstream introduced into the weathering chamber.

The black panel sensors, black standard sensors and white standard sensors used as temperature sensors are all designed such that they have a metal plate with a coated surface facing the light source during operation, and a temperature-dependent electric component coupled to the metal plate on the rear side thereof. The electric component is formed in this case as a rule by a temperature-dependent resistor such as a platinum resistor (commercial designations Pt100 or Pt1000), and is connected to an electric measuring transducer circuit.

In detail, a black standard sensor has a stainless steel plate (thickness 1 mm), coated black on one side, a Pt100 or Pt1000 resistor thermally coupled to the uncoated rear side, a plastic plate made from PVDF (polyvinylidene fluoride) and enclosing the platinum resistor, and a cover plate made from stainless steel. A white standard sensor is of corresponding design, with the difference that the surface facing the light source during operation has a white coating. By contrast with the black standard sensor, a black panel sensor comprises a metal plate blackened on both sides and without a PVDF insulation. The temperature-dependent resistor is applied to the rear side without a surrounding insulation.

In weathering devices according to the current standard, black standard or black panel sensors are used in order to be able to specify a black standard temperature for each weathering process. The black standard temperature constitutes an upper limit for the range under consideration from the surface temperature of the material sample. In addition, use is frequently made of a white standard sensor whose temperature measurement provides a lower limit of this range. It is thereby possible to delimit the sample temperature, and the arithmetic mean of the measured temperatures can be adopted, if appropriate, as first approximation for the sample temperature.

Before being taken into use, the above-described temperature sensors must be calibrated. The said black and white standard sensors and black panel sensors are currently calibrated using the so-called contact thermometry method, in each case a standard sensor being compared with a measuring sensor. In this case, two sensors of identical design are situated next to one another on a heating plate with the black (or white) coating on the heating plate. As an alternative thereto, it is also possible for both sensors to be put into an oil or water bath. The standard sensor has already been calibrated in advance in an oil or water bath by means of a standard thermometer such as a mercury thermometer, and therefore represents a temperature standard which can be ascribed to a PTB standard (PTB=German Federal Metrology Institute). Different temperatures are then produced on the heating plate (or in the oil or water bath). An output signal of the measuring transducer circuit, in which the platinum resistor of the temperature sensor to be calibrated is integrated, is then calibrated with the temperature measured with the aid of the standard temperature sensor.

A disadvantage of this conventional calibration method is that the calibration is carried out by excluding the parameters of xenon radiation, moisture and air movement, which are, however, precisely those factors which in reality determine the surface temperature in weathering devices or in outdoor weathering. Contact problems with the electric temperature sensors and relatively small differences in design which could lead to temperature differences in real conditions are not observed.

A further disadvantage of the conventional contact thermometry method consists in that the standard temperature sensor used in the process is itself to be equipped entirely as is the measuring temperature sensor to be calibrated, and must be calibrated as such. In accordance with the above described design, it must therefore have a platinum resistor which is thermally coupled to the rear side of the metal plate, and also the electric measuring transducer circuit associated therewith. So that it can be used as standard temperature sensor, it must be calibrated in an oil or water bath. The provision of the standard temperature sensor is therefore seen to be quite complicated.

It is consequently an object of the present invention to specify a method for calibrating a temperature sensor, in particular a temperature sensor which can be used in weathering devices, such as a black panel sensor, a black standard sensor or a white standard sensor, which method can be carried out with a reduced outlay. In particular, the aim of such a calibration method is to permit a simpler design of a reference or standard temperature sensor which may be used, or else to enable it to be omitted altogether. A further object of the calibration method consists in that it is to be suitable for being executed under conditions such as prevail inside the weathering chamber during operation of a weathering device.

These objects are achieved by means of the features of the independent Patent claim 1. Advantageous developments and modes of embodiment of the method according to the invention are specified in the subclaims. Apparatuses for carrying out the method according to the invention are likewise specified.

The temperature sensor to be calibrated can in this case be designed in a conventional way known per se, that is to say as a black panel sensor, black standard sensor or white standard sensor it can have the design described further above. The nature of the general form of the temperature sensor is that the latter has a temperature-dependent electric component included in an electric circuit such as a measuring transducer circuit. This component is preferably a temperature-dependent resistor, in particular a platinum resistor.

An essential idea of the present invention consists in that a contactless temperature measurement is carried out during the calibration. This contactless temperature measurement can be carried out either directly by the surface of the temperature sensor to be calibrated or by the surface of a reference temperature sensor. As is yet to be explained, this depends on the exact knowledge of a material property of the surface of the temperature sensor to be calibrated.

In detail, in the method according to the invention
 a) a variable temperature is produced on a surface of the temperature sensor to be calibrated and, if appropriate, on that of a reference temperature sensor,
 b) the temperature of the surface of the temperature sensor to be calibrated or of the reference temperature sensor is measured in a contactless fashion, and
 c) an output signal of the electric circuit is calibrated with the measured temperature.

The way in which the contactless temperature measurement is performed is preferably that in method step b) the blackbody radiation of the surface is measured and the temperature is determined therefrom. This can be performed with the aid of a conventional pyrometer which is calibrated at least in the measuring range corresponding to the temperature range of interest. The pyrometer is used in conjunction with a specific defined angle to affix a measuring spot on the surface of the temperature sensor to be calibrated or of the reference temperature sensor, and to detect the blackbody radiation emitted into the corresponding solid angle by this measuring spot, and to determine the surface temperature therefrom.

When the contactless temperature measurement is performed by measuring the blackbody radiation, this presupposes the principle that the emittance or emissivity of the surface material of the temperature sensor to be calibrated is known, since the surface, emitting the blackbody radiation, of the temperature sensor to be calibrated does not have the properties of an ideal blackbody radiator ($\epsilon=1$), and the emissivity $\epsilon$ is always smaller than 1. In particular, the angle of dependence of emissivity must also be known, since, as mentioned above, it is preferred for a pyrometer to detect the blackbody radiation radiated in a specific solid angle.

If the emissivity of the surface of the temperature sensor to be calibrated is known, the blackbody radiation emitted by it can be measured, and the surface temperature can be calculated therefrom. This surface temperature can then be used to calibrate the output signal of the electric circuit in which the platinum resistor is included. This would therefore have the great advantage that a calibrated reference temperature sensor which is essentially designed exactly like the temperature sensor to be calibrated would not need to be used.

However, another possible case is that the emissivity of the surface of the temperature sensor to be calibrated is not known. In fact, practical experience of coating materials obtained from black standard sensors or black panel sensors shows that, in particular, such black coatings which, owing to their high degree of resistance to ageing, are especially popular for use as coatings with black standard or black panel sensors, have emissivities which are not exactly known. Before the emissivity is determined in a complicated way, the method according to the invention can be carried out in such cases by using a reference temperature sensor having a surface with a known emissivity. In method step a) a variable temperature is produced both on the surface of the temperature sensor to be calibrated and on the surface of the reference temperature sensor under the same conditions so that it can be assumed that the surface temperatures of the two sensors are the same. In method step b), it is then necessary merely for the temperature of the surface of the reference temperature sensor to be measured in a contactless fashion, and this measured temperature can then be used in method step c) to calibrate the output signal of the electric circuit of the platinum resistor of the temperature sensor to be calibrated. If desired, it is also possible in parallel therewith further to measure the blackbody radiation of the temperature sensor to be calibrated such that it is possible by comparing the measurements of the blackbody radiations at the reference temperature sensor and at the temperature sensor to be calibrated in order to determine the emissivity of the surface of the latter.

When a reference temperature sensor must be used because of the unknown emissivity of the surface of the temperature sensor to be calibrated, the said reference temperature sensor does not, however, have the complicated design of the standard temperature sensor used in the conventional contact thermometry method. The reference temperature sensor to be used here does not, for example, require a thermally coupled temperature-dependent resistance element on the rear side together with an associated circuit. Instead of this, the reference temperature sensor can comprise merely a metal plate which is coated on one or both sides with the desired coating (black or white) of known emissivity. A reference temperature sensor of such a design constitutes for this variant embodiment of the method according to the invention a temperature standard which can be ascribed to a PTB standard.

The method according to the invention is further capable of being carried out under conditions such as typically prevail inside the weathering chamber of a weathering device currently in operation. This permits calibration of black and white standard sensors and of black panel sensors while these are being subjected to the parameters which occur during operation, such as optical radiation of the xenon lamp, air flow and moisture. These factors determine the surface temperature of the sensors in reality.

The conditions prevailing in a weathering device are largely determined, on the one hand, by the optical radiation of the xenon radiator. In order to provide approximately the same conditions for the calibration method according to the invention, it can therefore be provided in method step a) to produce the variable temperature by applying a radiation corresponding to the solar spectrum, in particular radiation of a xenon light source, to the surface of the temperature sensor and, if appropriate, that of the reference temperature sensor. Furthermore, it can be provided to produce just such an air movement of the surrounding air in the immediate vicinity of the surfaces of the sensors as is generated in weathering devices. It is possible accordingly to generate an airstream which flows past the sensors in a fashion parallel to the surfaces.

The above named conditions can ideally be provided by carrying out the calibration method in, or in conjunction with, an apparatus for the artificial weathering of samples.

Consequently the present invention further relates to apparatuses for carrying out the method according to the invention, corresponding to two different variants. In a first variant, a positioning apparatus is provided which has means for accommodating and holding the temperature sensor to be calibrated and, if appropriate, the reference temperature sensor, and means for holding the temperature sensor which measures in a contactless fashion, in particular the pyrometer. In order to carry out the calibration method, it is then necessary to ensure that the temperature sensor to be calibrated is fed heat, preferably by the application of radiant energy from a xenon radiation source. In a second variant, a commercial weathering device is converted so that the method according to the invention can be carried out therein. For this purpose, means are provided for accommodating and holding the temperature sensor to be calibrated and, if appropriate, the reference temperature sensor inside the weathering chamber, it also being possible for these means to be provided by the sample holder frame. Moreover, there is a need for means for fastening a contactless temperature sensor (such as a pyrometer) on an outer wall of the weathering chamber, as well as at least one opening in the outer wall such that the pyrometer can be aligned with the temperature sensors held in the weathering chamber.

Figure 2A:
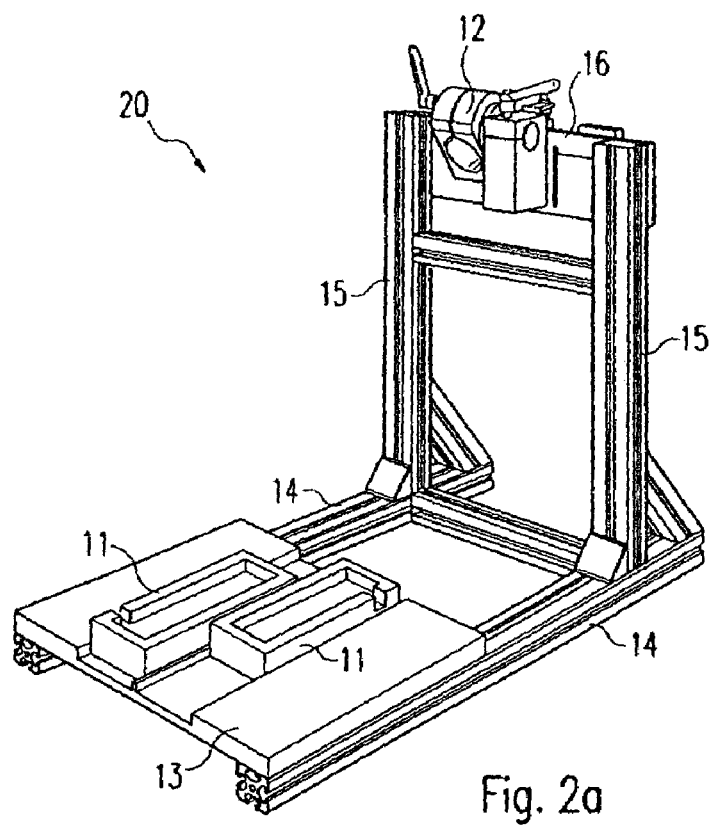
Figure 2B:
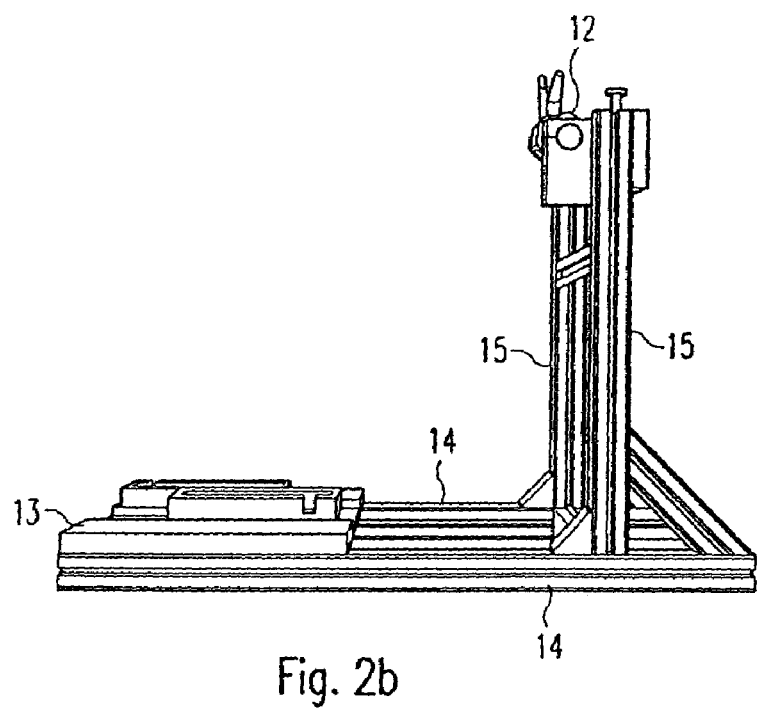
Figure 3:
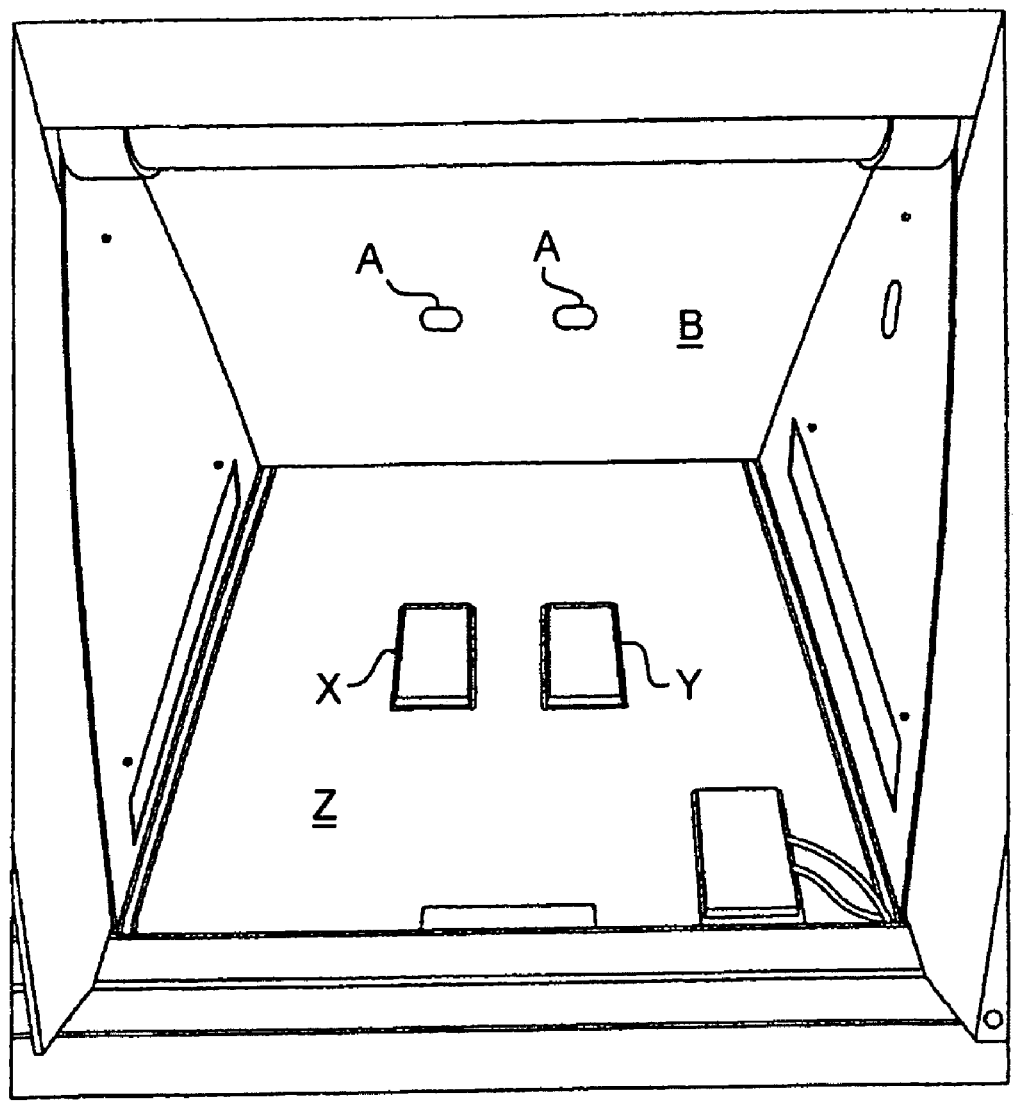

The invention is explained in yet more detail below with reference to the drawings, in which exemplary embodiments are shown and wherein:

FIG. 1 shows a longitudinal section through a black standard sensor to be calibrated;

FIG. 2a, b, c show a positioning apparatus as part of an apparatus for carrying out the calibration method, in a perspective view (a), in a side view (b) and in a front view (c); and FIG. 3 shows a partial view of the interior of a weathering device adapted for carrying out the calibration method.

A black standard sensor 10 such as is typically used in apparatuses for artificial weathering for monitoring the temperature of the material samples to be investigated is illustrated in FIG. 1. Such a black standard sensor 10 is held in this case in the immediate vicinity of the material samples with the same geometrical alignment as the latter with reference to the xenon radiation source. The black standard sensor 10 is illustrated in FIG. 1 in a longitudinal section along a plane running through the centre, that is to say the platinum resistor 3.

The black standard sensor 10 has a rectangular stainless steel plate 1 which is provided on one of its principle surfaces with a black coating 2. During the intended use of the black standard sensor 10, and also during calibration of the latter, the black coating 2 faces the xenon radiation source 7. Mounted on the unblackened rear side of the stainless steel plate 1 is a platinum resistor 3, it being assured that there is an optimum thermal coupling. In addition, a thermally insulating plastic plate 5 made from PVDF (polyvinylidenefluoride) is applied to the rear side of the stainless steel plate 1. At its centre, the plastic plate 5 has a cutout 5A which faces the stainless steel plate 1 and inside which the platinum resistor 3 is located. Adjoining the cutout 5A is a leadthrough 5B running up to the surface, averted from the stainless steel plate 1, of the plastic plate 5. The leadthrough 5B serves for feeding the electric feeder wires 4 to the platinum resistor 3. Via the feeder wires 4, the platinum resistor 3 is connected to a suitable electric circuit in which the resistance value of the platinum resistor 3 is converted into a current signal of 4–20 mA.

For the calibration, the optical radiation 7a of the xenon radiation source 7 which is not illustrated in FIG. 1 in a fashion true to scale with reference to the black standard sensor 10, is applied to the black standard sensor 10. As will be explained later, the calibration method can be carried out inside a weathering device with the xenon radiation source 7 contained therein. In addition, an airstream 9 is generated which flows past in the immediate vicinity of the surface of the metal plate 1, it being possible to generate the airstream 9 by means of a fan. As an alternative to this, or in addition, the black standard sensor can also be caused to rotate about the xenon radiation source 7 such that the airstream in this case directed perpendicular to the plane of the image comprises solely a relative movement between the black standard sensor 10 and the ambient air.

The contactless temperature measurement is performed by means of a conventional, calibrated pyrometer 8 which has a spectral sensitivity range of 8–14 µm. The pyrometer 8 detects the blackbody radiation emitted by a spot with a diameter of between 10 and 20 mm on the blackened surface of the stainless steel plate 1 in a solid angle 8a, and uses the said radiation to calculate the surface temperature taking account of the emissivity of the black coating 2. For the case where the emissivity of the black coating 2 of the temperature sensor 10 to be calibrated is not known, a reference temperature sensor with a black coating of known emissivity is arranged in the immediate vicinity of the temperature sensor 10 to be calibrated and measures the blackbody radiation by means of the pyrometer 8. The platinum resistor 3 or the output signal of the electric (measuring transducer)

circuit connected to it is calibrated with the surface temperature calculated therefrom.

The actual calibration operation, which is independent of the temperature measurement per se, is known in the prior art. As already mentioned, the platinum resistor 3 (Pt100 or Pt1000) is connected to a suitable electric circuit via the feeder wires 4. The said circuit can be, for example, a commercially available programmable measuring transducer circuit such as is commercially available from, for example, Dataforth Corporation of Tucson, Ariz., under the model number DSCP80.

Before the actual calibration operation, a resistor is firstly determined with the aid of a suitable measuring bridge. Tables which represent the relationship between the measured resistance and the temperature exist for the platinum resistors Pt100 or Pt1000. These curves can be approximated by polynomials. An analytical solution for the polynomial of the Pt100 curve does not exist, and for this reason calculation is frequently performed only up to the term second order when calculating t(R). The resistance value is converted with the aid of the programmable measuring transducer circuit into a current signal of 4–20 mA (or a digital signal), the lower value corresponding to 20° C., and the upper value 180° C. This measuring transducer circuit preprogrammed in such a way is then calibrated with the aid of the method according to the invention, calibration in this exemplary embodiment actually meaning setting and adjustment of the measuring transducer circuit to the temperature measured with the aid of the pyrometer. The essence of this procedure is to set sequentially two temperature values of the surface temperature by controlling the radiant power of the xenon radiation source 7. For example the radiant power is firstly set such that the pyrometer measures a lower value of 60° C. The DSCP80 measuring transducer is then set by means of an offset control such that it likewise indicates a temperature of 60° C. The radiant power is then increased so that the pyrometer indicates an upper value of 120° C. An amplification control of the DSCP80 measuring transducer is then used to set the latter such that it likewise indicates the temperature of 120° C. This process is to be executed iteratively several times in sequence, in some circumstances.

However, it has been shown in practice that the first setting is already sufficient and that two temperature values should further be approached only for checking purposes. If, however, deviations of greater than 1° C. are then determined, the calibration method must be carried out once again.

The following two possibilities exist in principle for carrying out the method according to the invention. Firstly, a suitable positioning apparatus can be provided on which, on the one hand, the temperature sensor to be calibrated and the reference temperature sensor and, on the other hand, the pyrometer can be positioned relative to one another in a reproducible way. The calibration then requires the provision of a radiation source in the vicinity of the temperature sensors, it also being possible for this purpose to bring a weathering device into the vicinity of the positioning apparatus. On the other hand, the method according to the invention can be carried out by converting an existing weathering device in a suitable way.

FIGS. 2a, b and c illustrate the first named variant from different directions of view. This variant is a positioning apparatus 20 which has two parallel horizontal profile rails 14 on which, at one of their ends, two vertical parallel profile rails 15 are fastened. Mounted on the horizontal profile rails 14 is a platform 13 which can be displaced along the profile rails 14 and be fastened on them at a desired position. Two cuboid accommodating blocks 11 are arranged next to one another on the platform 13 in such a way that they can be displaced in the direction of the profile rails 14 in guide channels which run parallel to the profile rails 14. On their upper sides, the accommodating blocks 11 each have rectangular depressions into which the temperature sensors can be laid. The accommodating blocks 11 can be fastened on the platform 13 at any desired position.

Figure 2C:
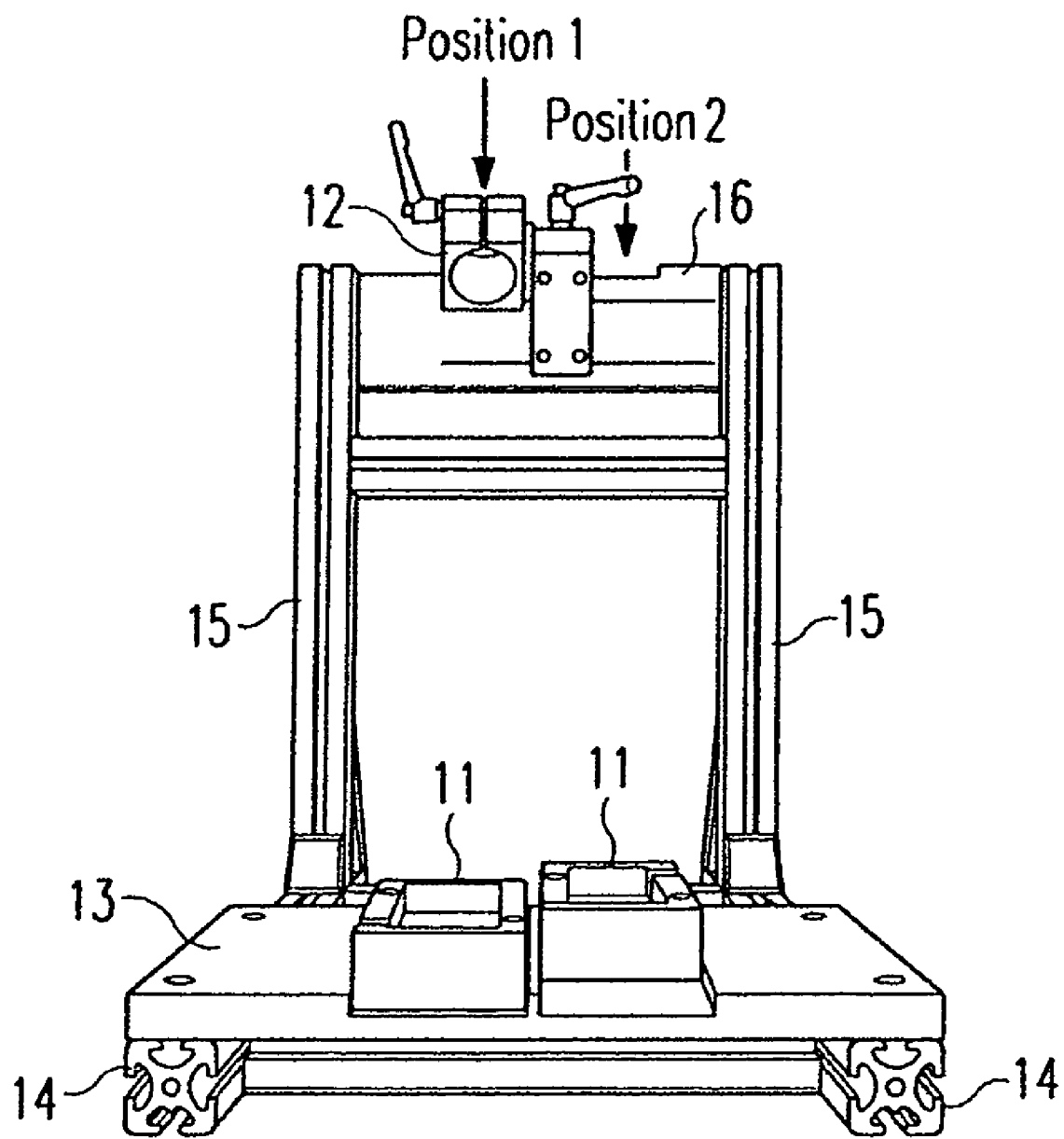

At their upper ends, the vertical profile rails 15 are connected to one another by a horizontal profile rail 16. It is possible to fasten in two positions on the top side of the horizontal profile rail 16 a clamping apparatus 12 for a pyrometer in which the pyrometer can be aligned with in each case one of the two temperature sensors positioned in the accommodating blocks 11, as is to be seen in particular in FIG. 2c. The clamping apparatus 12 essentially comprises a tubular cavity into which the pyrometer can be pushed from one side and can be clamped firmly therein.

With reference to the second named variant of carrying out the method according to the invention, an existing apparatus for artificial weathering of material samples is converted or adapted in such a way that the method according to the invention can be carried out thereby. This means in essence that accommodating and holding sections for the temperature sensors are provided inside the weathering device on one of the inner walls. FIG. 3 shows a perspective view of a part of the interior of an artificial weathering device. The temperature sensor to be calibrated X and the reference temperature Y sensor are posistioned one beside another on the horizontal lower inner wall Z. Formed in vertical inner wall B located in the longitudinal direction of the temperature sensor are two openings A through which the externally fastened pyrometer can be aligned with in each case one of the two temperature sensors X, Y. It suffices in principle thereby when only one opening A is formed in the housing wall B, since one contactless temperature measurement and one sensor suffices in principle during calibration. Either a temperature sensor to be calibrated X and having a known emissivity is located in the apparatus, and thus the temperature need be measured only at this sensor. If a reference temperature sensor X is additionally present according to an unknown emissivity of the temperature sensor to be calibrated X, all that is required is to measure the temperature at the said reference temperature sensor Y and calibrate it to the temperature sensor to be calibrated X. However, it is preferable to form two openings A so that there is the possibility from the very start of being able to use the externally fastened pyrometer to sight both accommodating regions for accommodating the temperature sensors. The pyrometer can be fastened from outside with the aid of a spring latch or the like.

The invention claimed is:

1. A method for calibrating a temperature sensor, namely a black temperature panel sensor, a black standard temperature sensor or a white standard temperature sensor, wherein
the temperature sensor is comprised of a plate which is coated on at least one side with a black or white coating and a temperature-dependent electric component which is included in an electric circuit and which is thermally applied to the plate, the method comprising:
producing a variable temperature on a surface of the plate by applying a radiation corresponding to the solar spectrum on the surface of the plate,
measuring the temperature of the surface of the plate in a contactless fashion, and
calibrating an output signal of the electric circuit with the measured temperature.

2. The method according to claim 1, wherein the blackbody radiation of the surface, and the temperature is determined therefrom.

3. The method according to claim 2,
emissivity of the surface of the temperature sensor to be calibrated is known, and
the blackbody radiation of the temperature sensor to be calibrated is measured, and the temperature is determined therefrom taking account of the emissivity.

4. The method according to claim 2, wherein
the emissivity of the surface of the temperature sensor to be calibrated is not known, and
the blackbody radiation of the reference temperature sensor is measured, and the surface temperature is determined therefrom taking account of the known emissivity of the surface of the reference temperature sensor.

5. The method according to one of claim 2, 3, or 4, wherein measuring the blackbody radiation is carried out with the aid of a calibrated pyrometer, in particular at a defined solid angle to the surface.

6. The method according to claim 2, wherein the blackbody radiation emitted by the surface within a defined solid angle is measured.

7. The method according to claim 1, wherein producing the variable temperature includes applying a radiation corresponding to the solar spectrum to the surface of the temperature sensor.

8. The method according to claim 1, wherein an airstream parallel to the surface is generated in the region of the surface of the temperature sensor.

9. A positioning apparatus for holding temperature sensors for carrying out the method according to claim 1, the positioning apparatus comprising:
means for accommodating and holding the temperature sensor to be calibrated and the reference temperature sensor, and
means for holding the contactless temperature sensor.

10. The Positioning apparatus according to claim 9, further comprising:
horizontal rails on which there rests a platform with accommodating blocks for accommodating the temperature sensor to be calibrated and the reference temperature sensor, and
vertical rails which are fastened on the horizontal rails and between which a clamping apparatus for the contactless temperature sensor is fastened.

11. An apparatus for carrying out the method according to claim 1, the apparatus comprising:
a positioning apparatus according to claim 9,
a contactless temperature sensor held by the holding means, and
means for feeding thermal energy to the temperature sensor to be calibrated and to the reference temperature sensor.

12. An apparatus for artificially weathering samples, which is converted for carrying out the method according to claim 1, the apparatus comprising:
means for accommodating and holding the temperature sensor to be calibrated and the reference temperature sensor,
means for fastening a contactless temperature sensor on an outer wall of the apparatus, and
at least one opening in the outer wall which is such that the fastened contactless temperature sensor can be aligned through the opening with the temperature sensor to be calibrated or with the standard temperature sensor.

13. A method for calibrating a temperature sensor by use of a reference temperature sensor, wherein
the temperature sensor is comprised of a first plate and a temperature-dependent electric component which is included in an electric circuit, wherein the emissivity of the surface of the first plate is unknown, and
a reference temperature sensor is comprised of a second plate, wherein the emissivity of the surface of the second plate is known;
the method comprising:
producing a variable temperature on the surface of the first plate of the temperature sensor and on the surface of the second plate of the reference temperature sensor by applying a radiation corresponding to the solar spectrum simultaneously to the surface of the first plate and to the surface of the second plate,
measuring the temperature of the surface of the second plate of the reference temperature sensor in a contactless fashion, and
calibrating an output signal of the electric circuit with the measured temperature.

14. A method for calibrating a temperature sensor for use in an apparatus for the artificial weathering of samples, wherein
the temperature sensor is comprised of a plate and a temperature-dependent electric component included in an electric circuit,
the method comprising:
providing an apparatus for the artificial weathering of samples, the apparatus comprising a chamber and a radiation source for the emission of radiation corresponding to the solar spectrum,
producing a variable temperature on a surface of the plate of the temperature sensor by placing the temperature sensor inside the chamber of the apparatus such that the surface of the plate is directed towards the radiation source,
measuring the temperature of the surface of the plate in a contactless fashion, and
calibrating an output signal of the electric circuit with the measured temperature.

* * * * *